(12) United States Patent
Klopffer et al.

(10) Patent No.: US 9,134,278 B2
(45) Date of Patent: Sep. 15, 2015

(54) METHOD FOR TESTING THE INTEGRITY OF A FLEXIBLE TUBULAR PIPE

(75) Inventors: Marie-Hélène Klopffer, Montigny-le-Bretonneux (FR); Xavier Lefebvre, Conflans-Sainte-Honorine (FR); Yann Nicolas, Grenoble (FR); Patrice Jung, La Maillaraye sur Seine (FR)

(73) Assignees: Technip FRANCE (FR); IFP ENERGIES NOUVELLES (FR)

( * ) Notice: Subject to any disclaimer, the term of this patent is extended or adjusted under 35 U.S.C. 154(b) by 376 days.

(21) Appl. No.: 13/808,831

(22) PCT Filed: Jul. 5, 2011

(86) PCT No.: PCT/FR2011/051574
§ 371 (c)(1),
(2), (4) Date: Jan. 31, 2013

(87) PCT Pub. No.: WO2012/004508
PCT Pub. Date: Jan. 12, 2012

(65) Prior Publication Data
US 2013/0125655 A1 May 23, 2013

(30) Foreign Application Priority Data
Jul. 8, 2010 (FR) .................................. 10 55557

(51) Int. Cl.
*G01N 29/04* (2006.01)
*F16L 11/08* (2006.01)
(Continued)

(52) U.S. Cl.
CPC ............ *G01N 29/043* (2013.01); *F16L 11/083* (2013.01); *F16L 57/00* (2013.01);
(Continued)

(58) Field of Classification Search
CPC .......................... G01N 29/07; G01N 2291/044
USPC ..................................... 73/590, 592, 597, 598
See application file for complete search history.

(56) References Cited

U.S. PATENT DOCUMENTS

| 5,038,615 A | 8/1991 | Trulson et al. |
| 5,225,148 A | 7/1993 | Desruelles |

(Continued)

FOREIGN PATENT DOCUMENTS

| EP | 0 844 429 | 5/1998 |
| FR | 2 835 317 A1 | 8/2003 |

(Continued)

OTHER PUBLICATIONS

International Search Report and Written Opinion dated Dec. 8, 2011 issued in corresponding international patent application No. PCT/FR2011/051574.

*Primary Examiner* — John Chapman, Jr.
(74) *Attorney, Agent, or Firm* — Ostrolenk Faber LLP

(57) ABSTRACT

Method for testing a pipe for carrying hydrocarbons. The pipe has at least one internal sealing sheath made of polymer material, incorporating elements of reactive compound capable of reacting with corrosive gases contained in the hydrocarbons which diffuse radially through the sheath. The reaction forms a first layer, extending radially from the internal surface, in which the elements of reactive compound have reacted with the gases. A second layer, extends between the first layer and the external surface, in which the elements of reactive compound have not yet reacted with the gases. The method uses ultrasound to determine the position of an interface between the first and second layers to measure the progression of the diffusion of the gases through the sheath.

9 Claims, 3 Drawing Sheets

(51) Int. Cl.
*F16L 58/10* (2006.01)
*F17D 5/06* (2006.01)
*G01M 3/24* (2006.01)
*G01N 29/07* (2006.01)
*F16L 57/00* (2006.01)
*F16L 11/04* (2006.01)

(52) U.S. Cl.
CPC ............... *F16L 58/1009* (2013.01); *F17D 5/06* (2013.01); *G01M 3/24* (2013.01); *G01M 3/243* (2013.01); *G01N 29/07* (2013.01); *F16L 2011/047* (2013.01); *G01N 2291/0245* (2013.01); *G01N 2291/0289* (2013.01); *G01N 2291/044* (2013.01); *G01N 2291/2634* (2013.01)

(56) References Cited

U.S. PATENT DOCUMENTS

| | | | |
|---|---|---|---|
| 6,378,375 | B1 | 4/2002 | Kobayashi |
| 2007/0193357 | A1 | 8/2007 | Daaland et al. |
| 2009/0064770 | A1 | 3/2009 | Olsen et al. |

FOREIGN PATENT DOCUMENTS

| | | |
|---|---|---|
| GB | 2 462 078 | 1/2010 |
| WO | WO 00/77587 | 12/2000 |
| WO | WO 2009/106078 A1 | 9/2009 |

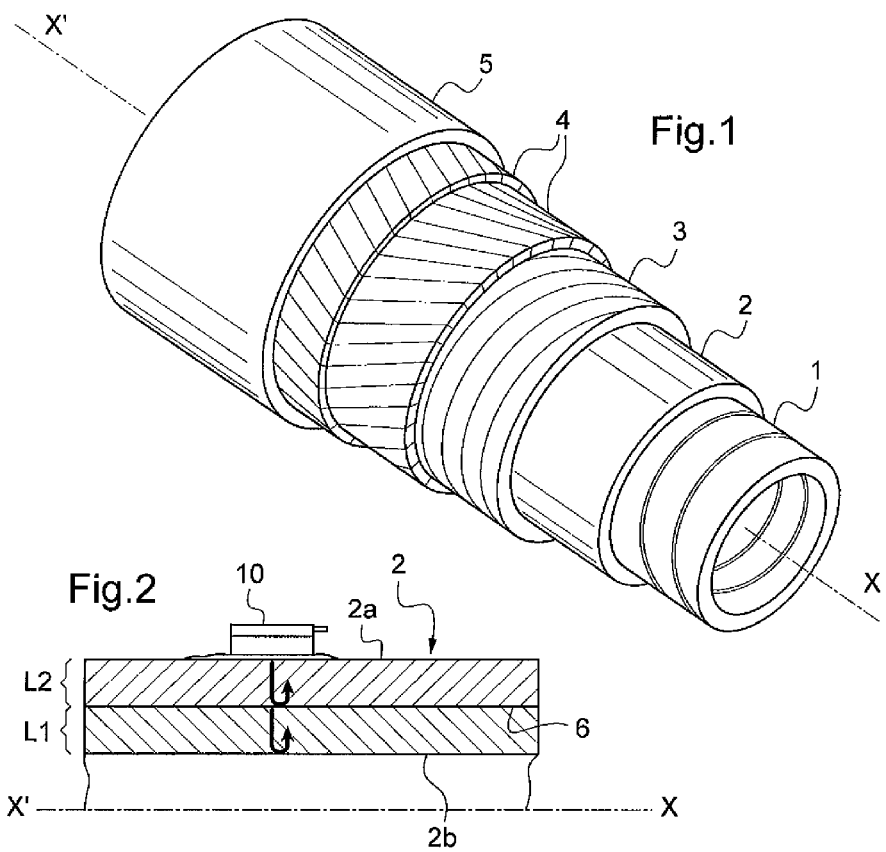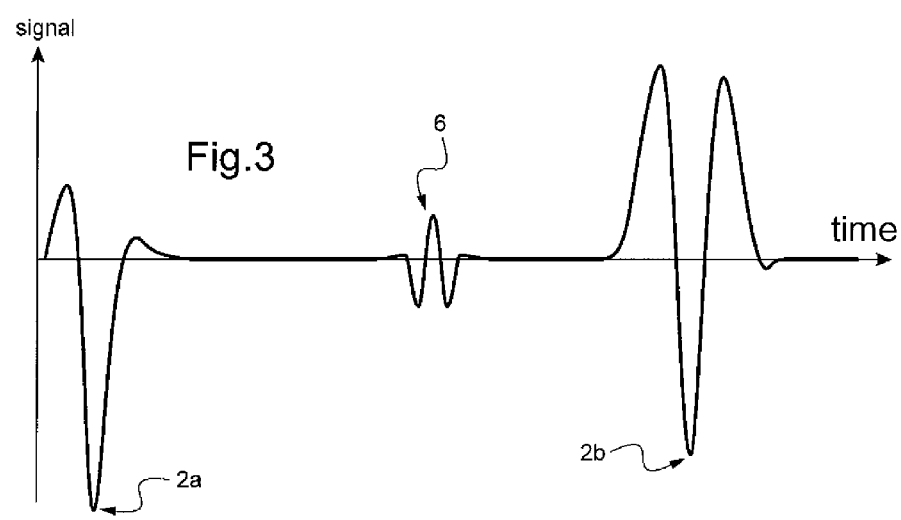

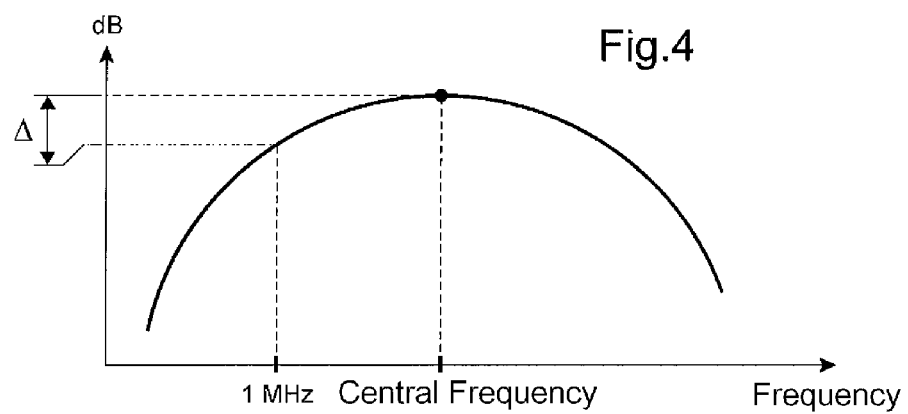
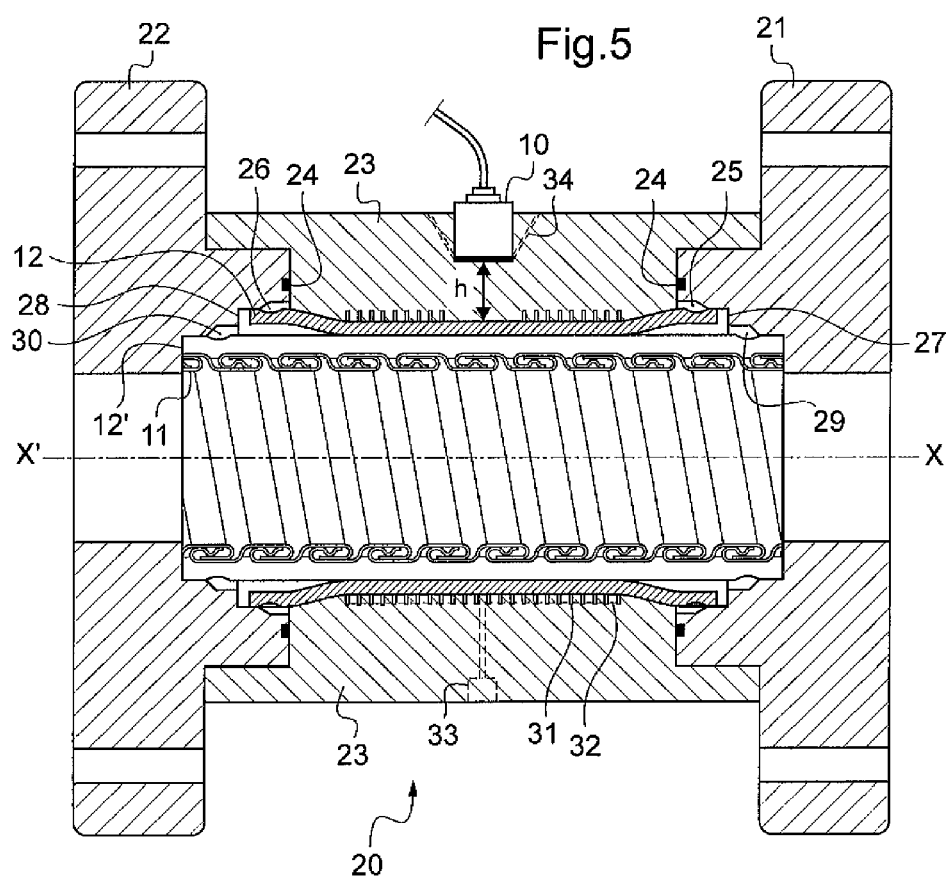

METHOD FOR TESTING THE INTEGRITY OF A FLEXIBLE TUBULAR PIPE

CROSS-REFERENCE TO RELATED APPLICATIONS

The present application is a 35 U.S.C. §§371 national phase conversion of PCT/FR2011/051574, filed Jul. 5, 2011, which claims priority of French Application No. 1055557, filed Jul. 8, 2010, the contents of which are incorporated by reference herein. The PCT International Application was published in the French language.

The present invention relates to the field of monitoring tubular pipes especially intended to be used by the offshore drilling industry, for example to transport hydrocarbons. It more particularly relates to a method used to inspect the integrity of such a pipe with respect to the action of aggressive fluids, especially corrosive gases, for example $H_2S$ and $CO_2$ present in the hydrocarbons transported by the pipe.

The invention especially targets flexible submarine pipes intended to transport hydrocarbons the pressure and temperature of which may reach 1000 bar and 130° C., respectively. Such a flexible pipe, in its general form, is well known in the art and takes various configurations depending on its exact use but generally meets the structural criteria especially defined in standards API 17 RP B and API 17J established by the American Petroleum Institute under the titles "Recommended Practice for Flexible Pipe" and "Specification for Unbonded Flexible Pipe".

A common type of such flexible oil and gas pipes comprises, from the interior to the exterior: an internal carcass of interlocking metal strips intended to prevent the pipe from being crushed; an internal sheath made of an extrudable thermoplastic, generally a polymer, bearing against the carcass and intended to provide the pipe with an internal seal; a set of metal armor layers intended to withstand compressive and/or tensile stresses; and an external sheath that protects and seals, made of a thermoplastic, generally a polymer.

An inherent problem with the transportation of hydrocarbons in these pipes, in particular at high temperatures and pressures, is related to the permeability of the internal sheath to corrosive fluids. Specifically, gases such as $H_2S$ are able to diffuse through the thermoplastics used to fabricate the sheaths, and it is known that the flow rate of gas through thermoplastics increases with temperature and pressure. Now, $H_2S$ is a gas that corrodes unalloyed or low-alloy carbon steels from which the various metal armor layers present in the annular cavity, located between the two, internal and external, sheaths, in the pipe, are usually made. Therefore, when such corrosive gases diffuse through the internal sheath and penetrate into the annular cavity located between the internal and external sheaths, the metal armor layers of the pipe may, under certain conditions, undergo corrosion which may eventually have a critical effect on the integrity of the pipe.

One of the solutions envisioned to solve this problem of corrosion consists in placing intermediate between the hydrocarbon flowing through the pipe and the metal armor layers a sheath made of a polymer incorporating a reactive compound, the latter being dispersed through said polymer, this reactive compound being able to react with the acidic gases in order to neutralize them. In this way, the sheath is sealed with respect to the gases in question.

Document EP 0 844 429 describes such a solution. The sealing barrier layer is an extruded sheath made of polyethylene filled with fine particles of zinc oxide (ZnO). This reactive ZnO compound reacts with $H_2S$ so as to neutralize it, forming ZnS, which remains trapped in the sheath, and water ($H_2O$) that diffuses through the sheath. This solution is very effective provided that some reactive compound remains in the barrier layer. However, it has the drawback of having a limited lifetime, since it loses its effectiveness once all of the reactive ZnO compound has reacted with $H_2S$. From this moment on, $H_2S$ can freely diffuse through the barrier layer and reach the metal armor layers of the flexible pipe. Corrosion of the metal armor layers may then greatly accelerate, thereby risking a significant reduction in the remaining lifetime of the pipe. Specifically, the metal armor layers of these pipes are not designed to withstand, for any length of time, the rate of corrosion that they would have to endure in the absence of the barrier layer; hence, if this barrier layer abnormally and prematurely loses its seal, the remaining lifetime of the pipe would be substantially shortened.

Although the lifetime of such a barrier layer can be evaluated using an experimentally validated theoretical physical model, it is nevertheless desirable to instrument the flexible pipe with means not only allowing the correct operation of the barrier layer to be checked in real time, but also allowing its remaining lifetime to be accurately predicted. This is because replacing a pipe is a very complex and expensive operation which requires production to be stopped and which is liable to lead to very large additional costs if not correctly predicted and planned for.

A method for monitoring a pipe of the aforementioned type, based on an analysis, using spectroscopic techniques, of the chemical composition of the fluids present in the annular cavity between the internal and external sheaths of the pipe, is known from document WO 2009/106078. The method described in this document thus makes it possible to effectively detect the presence of corrosive gases coming from the hydrocarbons transported by the pipe and having penetrated into the annular cavity through the internal sheath, by means of which a threat to the safety of the pipe may rapidly be diagnosed.

However, this method for monitoring a pipe is not completely satisfactory in that, although it allows, by delivering information regarding the presence of corrosive gases in the annular cavity, an immediate risk of accelerated corrosion of the metal armors layer of the pipe to be diagnosed, it does not, in contrast, allow the onset of this problem to be predicted. Specifically, since the measurement is carried out in the annular cavity, when corrosive gases are detected they are already in contact with the metal armor layers and corrosion may therefore, under certain conditions, have already started.

In this context, the aim of the present invention is to provide a method and a device for monitoring a pipe of the aforementioned type, meeting this need and which may provide an early indication of the remaining lifetime of the pipe.

The invention achieves this aim by providing a method for monitoring a tubular pipe intended to transport hydrocarbons containing corrosive gases, said pipe comprising at least one internal polymer sheath into which said corrosive gases are liable to diffuse radially from an inner surface to an outer surface of said internal sheath via a radial diffusion effect, said polymer of said internal sheath incorporating reactive-compound elements dispersed through the thickness of said internal sheath and able to react with said corrosive gases in order to neutralize them via a neutralizing reaction, said neutralizing reaction and said radial diffusion effect forming, on the one hand, a first layer, in said internal sheath, in which said reactive-compound elements have reacted with said corrosive gases, said first layer gradually extending through the thickness of said internal sheath from said inner surface and, on the other hand, a second layer occupying the residual thickness of said internal sheath, in which layer said reactive-compound elements have still not reacted with said corrosive gases, said second layer extending between said first layer and said outer surface of said internal sheath, noteworthy in that the position of an interface between said first layer and said second layer occupying some thickness of said internal sheath is determined using ultrasound, so as to measure, in real time, the progression of the diffusion of said corrosive gases through the thickness of said internal sheath.

When ultrasonic waves meet an interface bounding two media having different acoustic impedances, the waves are reflected giving rise to an echo according to the principle of ultrasonography, well known in medical imaging for example.

By applying this principle, the method of the invention allows the position of an interface representing the advance of a front of conversion of the reactive-compound elements dispersed through the thickness of the sheath, after a chemical reaction with the corrosive gases gradually diffusing through the thickness of the sheath, to be located, the advance of this front of conversion of these reactive-compound elements then serving as a marker for quantifying the advance of the corrosive gases through the thickness of the sheath. Specifically, this conversion front, which is located at the inner surface of the internal sheath at the start of the life of the pipe, then progresses over time through the thickness of the sheath, in order to finish at its outer surface when all the reactive-compound elements have been consumed via chemical reaction with the corrosive gases, advantageously bounds two layers occupying some thickness of the internal sheath, respectively a first layer extending gradually through the thickness of the sheath from its inner surface and consisting of a mixture of the polymer and the products of the chemical reaction between the reactive-compound elements and the corrosive gases, and a second layer occupying a residual thickness, extending between the first layer and the outer surface of the sheath and consisting of a mixture of the polymer and the intact reactive-compound elements that have not yet been reached by the corrosive gases.

The use of the ultrasonography principle recalled above to detect and locate the interface between these two layers occupying gradually changing thicknesses in the internal sheath, will, prima facie, be of great surprise to those skilled in the art.

This is because the materials of these two layers occupying some thickness have mechanical properties that are very similar to those of the polymer forming the sheath, and therefore there is very little difference between them, on account of the small amount of the products produced by the chemical reaction and of the reactive-compound elements present, respectively, in the first and second layers. It is a priori clear that, with mechanical properties that are so similar, it would not, based on common knowledge, be possible to envision that a transition between the materials forming these two layers occupying some thickness in the sheath would generate an ultrasound echo allowing the position of any interface between these two layers to be detected and located, and a person skilled in the art would therefore discard the idea of using an ultrasonography method for this purpose.

According to the invention, it has been discovered that the chemical reaction between reactive-compound elements dispersed through the thickness of the sheath and corrosive gases diffusing through the sheath, forming a first layer that extends gradually through the thickness of the sheath from its inner surface, is nevertheless enough to sufficiently modify the mechanical properties of this first layer of the sheath, relative to those of the second layer occupying a residual thickness in the sheath and extending between this first layer and the outer surface of the sheath, that it is indeed possible to use an ultrasound monitoring method to detect and locate the interface between these two layers and thus to quantify, in real time, the advance of the front of conversion of the reactive-compound elements, revealing the advance of the diffusion of corrosive gases through the thickness of the sheath, by means of which it is possible to predict the remaining lifetime of the pipe.

To do this, an ultrasound beam is emitted, from the outer side of the internal sheath in the direction of the interior of the pipe, so that the ultrasound beam passes through the thickness of the internal sheath between its outer surface and its inner surface, the ultrasonic waves reflected in the thickness of said sheath by said interface are collected, in the form of signals, and said signals are processed so as to determine the position of said interface in the thickness of said internal sheath.

Advantageously, the central frequency of the ultrasound beam lies between 1 and 5 MHz, preferably between 1.5 and 3 MHz, advantageously between 2 and 2.5 MHz, and more advantageously is about 2.25 MHz. Advantageously, the pulse width, measured at −20 dB, lies between 0.5 and 1.5 µs and is advantageously smaller than 1 µs. Advantageously, the bandwidth, measured at −6 dB, lies between 1 and 4 MHz, and a spectrum is used comprising a sufficiently large number of waves with a low frequency of about 1 MHz the amplitude difference of which, relative to the central frequency, must not be less than 30 dB.

Again advantageously, the shape of the ultrasound beam is focused and the beam focal point is positioned toward or beyond the bottom of said internal sheath.

The ultrasound transducer is a piezoelectric transducer and is preferably a piezocomposite transducer. In this case it is advantageous for a focus to be achieved by shaping the piezocomposite component itself.

Advantageously, a square-shaped or annular two-dimensional array of elementary transducers is used. In this case, the ultrasound beam is preferably controlled using an electronic phase-shift technique.

Furthermore, advantageously, the reactive compound is chosen from ZnO, PbO, CuO, CdO, NiO, $SnO_2$ and $MoO_3$.

According to a first embodiment of the invention, the tubular pipe may be a flexible pipe. The term "internal sheath" must then be understood with a wide sense as denoting any type of internal sheath of the flexible pipe. Specifically, the reactive-compound elements may be incorporated either into the first sheath starting from the interior of the pipe, or into an intermediate sheath located between, on the one hand, this first sheath and, on the other hand, the external sheath.

According to a second embodiment of the invention, the tubular pipe may be a rigid pipe, and especially a rigid pipe comprising an internal polymer sheath surrounded by a metal tube. The polymer sheath has the function of lining the interior of the metal pipe in order to protect it from corrosion. This type of pipe is especially described in document WO 00/77587. The protection provided by the internal polymer sheath or liner may be improved by incorporating a reactive agent into the polymer used to form said liner. In this case, the present invention allows the advance of the diffusion of acidic gases into the liner to be monitored and the moment when these gases will reach the inner wall of the metal tube to be predicted.

The invention also relates to a monitoring section able to be attached to a tubular pipe intended to transport hydrocarbons containing corrosive gases, noteworthy in that it comprises, from the interior to the exterior, a number of coaxial layers and especially at least one internal sheath and a cylindrical metal cover fitted around said internal sheath, said internal sheath being made of a polymer incorporating reactive-compound elements dispersed through the thickness of said sheath and able to react with corrosive gases in order to neutralize them, said corrosive gases being liable to diffuse radially from an inner surface toward an outer surface of said internal sheath, thereby forming, on the one hand, a first layer in which said reactive-compound elements have reacted with said corrosive gases, said first layer gradually extending through the thickness of said sheath from said inner surface and, on the other hand, a second layer occupying the residual thickness of said sheath, in which second layer said reactive-compound elements have still not reacted with said corrosive gases, said second layer extending between said first layer and said outer surface of said sheath, said monitoring section comprising an integrated ultrasonic transducer able to determine the position of an interface between said first layer and said second layer occupying some thickness of said sheath using ultrasound so as to measure, in real time, the progression of the diffusion of said corrosive gases through the thickness of said internal sheath.

It is difficult to integrate an ultrasound sensor in an oil and gas pipe of great length, particularly when the latter is a flexible pipe comprising many layers. It is thus simpler to produce a short instrumented section, taking care to ensure that this section has a structure representative of the main pipe as regards diffusion and neutralization of the acidic gases, and to then connect this section in series with the main, flexible or rigid, pipe so as to form a transportation pipe according to the present invention.

Preferably, the ultrasonic transducer is housed in the cylindrical metal cover, the residual thickness of the cover left between the front side of the transducer and the outer surface of the internal sheath being larger than at least three times the thickness of said sheath.

Advantageously, first means are provided for coupling the front side of the ultrasonic transducer to the cylindrical metal cover and second means for coupling the outer surface of the internal sheath to the cylindrical metal cover.

Advantageously, the second coupling means comprise pressurized means for mechanically coupling the outer surface of the internal sheath to an inner surface of the cylindrical metal cover.

The cylindrical metal cover may comprise a circuit for draining gases diffusing through the internal sheath, said draining circuit comprising a set of grooves formed on an inner surface of said cover at an interface with an outer surface of the internal sheath, said set of grooves being connected to an aperture able to be closed by a removable blocking means and communicating with the exterior of said monitoring section, by means of which the pressure to which said internal sheath is subjected may be controlled.

Advantageously, the monitoring section comprises two connecting flanges respectively fitted at either end of said cylindrical metal cover and on which flanges crimping cones are arranged to bear against said internal sheath.

The invention also relates to a pipe intended to transport hydrocarbons containing corrosive gases, said pipe comprising at least one monitoring section of the invention, noteworthy in that said pipe comprises at least one internal sheath similar to that fitted in said monitoring section, by means of which it is possible to monitor the progression of the diffusion of the corrosive gases through the thickness of said internal sheath of said pipe.

Other features and advantages of the invention will become apparent on reading the following description of a particular embodiment of the invention, given by way of nonlimiting indication and with reference to the appended figures, in which:

FIG. 1 is a partial perspective view of one embodiment of a flexible pipe that can be used to transport hydrocarbons;

FIG. 2 is a schematic longitudinal cross-sectional view of an internal sheath inspected according to the invention and an ultrasound inspection transducer;

FIG. 3 is an example of an echogram obtained during inspection of the sheath using the method of the invention;

FIG. 4 shows the emission spectrum of the ultrasound beam used;

FIG. 5 shows a longitudinal cross section through a pipe monitoring section, intended to be placed in series with the flexible pipe and instrumented according to the invention;

Figure 6A:
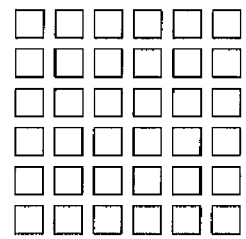
FIGS. 6a and 6b illustrate two examples of possible configurations for arrays of elementary transducers possibly suitable for producing the ultrasound transducer of the monitoring section according to the invention.

FIG. 1 represents a flexible rough-bore pipe 10 comprising, from the interior to the exterior: an internal carcass 1 made of profiled metal strip or wire, with interlocked turns wound with a short pitch, intended to prevent the pipe from being crushed under external pressure; at least one internal polymer sheath 2, also called the pressure sheath; a structural assembly of metal armors here comprising a pressure vault 3 and tensile armor layers 4; and the external protective sheath 5.

The invention does not depend on the precise configuration of the pipe, it may be implemented in pipes other than pipes of the type illustrated in FIG. 1, for example it may be implemented in a flexible pipe with a smooth internal passage (called smooth-bore pipes) where the passage is formed directly by the internal sheath without a carcass being present therein. Thus, the description of the pipe is given merely by way of indication of one possible embodiment in which the invention may be implemented.

The internal sheath 2 is made of an extrudable plastic and generally of a polymer. It may, for example, be made of polyethylene, polyolefin, polyamide or of a fluoropolymer.

According to the invention, the sheath 2 comprises a preset amount of a reactive compound that is able to react chemically with the corrosive gases present in the hydrocarbons transported, these gases being liable to diffuse radially through the internal sheath from its inner surface towards its outer surface, the reactive compound thus acting as a marker marking the advance of the corrosive gases through the sheath, as will be explained in greater detail below.

The invention is based on known chemical reactions, used in the field of methods for filtering corrosive gases especially as a result of the presence of $H_2S$ and $CO_2$, but which have at no point ever been used for the purpose of monitoring the diffusion of corrosive gases through the thickness of a sheath in the field of flexible pipes for transporting hydrocarbons.

Among the reactive compounds that can be used for the purpose of the invention, mention may be made of those comprising metal oxides such as ZnO, which reacts with $H_2S$ via the following reaction:

$$ZnO + H_2S \rightarrow ZnS + H_2O. \qquad (1)$$

Among other reactive compounds of the same type, mention may also be made, for example, of PbO, CuO, CdO, NiO, $SnO_2$, $MoO_3$ and the associated carbonate forms.

Thus, according to one embodiment, the internal sheath 2 is manufactured using a mixture prepared at the melting point of polyethylene by adding the reactive compound, for example a metal oxide such as ZnO, before extrusion. In this way, the internal polyethylene sheath 2 produced contains the reactive compound, for example a metal oxide, dispersed throughout the thickness of the sheath.

The principle on which the invention is based is then detection and location of the interface between the reactive compound, for example the ZnO, and the reactive compound having reacted with $H_2S$, for example ZnS, in the sheath via an ultrasonography method, in order to measure the advance of the diffusion of the corrosive gas through the thickness of the sheath.

FIG. 2 shows in detail the internal polyethylene (PE) sheath 2 containing the reactive compound, for example ZnO, dispersed through its thickness. A partial cross section of the sheath 2, which is symmetric about its longitudinal axis XX', the latter coinciding with the central axis of the pipe, is shown. The pipe is instrumented with an ultrasound transducer 10 that is coupled to the sheath 2 so as to emit, radially to the pipe, an ultrasound beam that passes through the thickness of the sheath and is reflected, to a greater or lesser extent, by obstacles and, in particular, the outer surface 2a of the sheath (top of the sheath), the inner surface of the sheath 2b (bottom of the sheath), and the interface 6 between the reactive compound, for example ZnO, and the reactive compound having reacted with $H_2S$, for example ZnS, embodying the advance over time of the front of conversion of the ZnO into ZnS through the thickness of the sheath, from the inner surface 2b toward the outer surface 2a under the effect of the diffusion of corrosive gases through the thickness of the sheath.

Specifically, when the pipe is in use, corrosive gases such as $H_2S$ present in the hydrocarbons transported by the pipe diffuse radially from the inner surface 2a toward the outer surface 2b of the internal sheath 2 and thus form a diffusing-gas layer L1 that gradually extends from the inner surface 2a through the thickness of the sheath, in which diffusing-gas layer the reactive compound, for example ZnO, reacts with the diffusing corrosive gases via the chemical reaction (1), whereas a layer L2 occupying the residual thickness of the sheath, as yet unreached by the diffusing corrosive gases, extends between the layer L1 and the outer surface 2b of the sheath.

The layer L1 mainly consists of PE and of reactive compound having reacted with the $H_2S$, for example ZnS, the latter resulting from the chemical reaction between the ZnO and the diffusing corrosive gases, whereas the layer L2 mainly consists of PE and reactive compound, for example ZnO, the latter yet to be consumed by the chemical reaction because the corrosive gases have yet to diffuse into this layer.

Therefore, the two layers L1 and L2 of the internal sheath have acoustic impedances that differ, respectively, so that it is possible to detect the interface 6 bounding these two layers by reflecting ultrasonic waves from this interface, and thus to measure the progression of the diffusion of the $H_2S$ through the PE+ reactive compound forming the sheath.

The amount of reactive compound that needs to be incorporated into the polyethylene to manufacture the sheath must therefore be determined in order to guarantee a sufficiently significant difference between the mechanical properties of, on the one hand, the PE+ reactive compound, and on the other hand, the PE+ reactive compound having reacted with $H_2S$, so as to allow the interface separating these two layers of material in the sheath to be detected by the ultrasonography method.

The ultrasound signals reflected in the thickness of the internal sheath 2 appear on the echogram illustrated in FIG. 3, giving the return signal received as a function of time for the embodiment in FIG. 2, where the sheath is made of PE and ZnO and a front of conversion of ZnO to ZnS progresses, over time, through the thickness of the sheath from its inner surface 2b. These reflected ultrasound signals allow obstacles 2a, 2b and 6 to be detected. Thus the position and amplitude of the echoes from the top of the sheath 2a, from the bottom of the sheath 2b and from the interface 6 embodying the front of conversion of the ZnO to ZnS, are recorded.

It will be noted that the echo from the bottom of the sheath and echo from the interface have inverse polarities. This feature will advantageously be used to obtain a certain identification of the interface echo, even in the presence of a high noise level.

The advance of the front of conversion of the ZnO to ZnS, and therefore the progression of the diffusion of the gases through the thickness of the sheath, may thus be easily measured by calculating the ratio of the time-of-flight measured for the echo from the interface of the front to that measured for the echo from the bottom of the sheath. Thus, this measurement is temperature independent if the temperature is uniform through the thickness of the sheath.

The location of the echoes from the top and bottom of the sheath also allow the thickness of the sheath to be checked.

FIG. 2 is simply meant to illustrate the above interface detection principle, and is therefore intentionally schematic, especially with regard to details of how the ultrasound transducer is fitted to the pipe, particulars of which will be provided in the description below especially with reference to FIG. 5.

Moreover, it will be noted that it is already known, from patent document EP 0 844 429, to use the chemical reaction (1) mentioned above to manufacture internal sheaths in the field of flexible pipes, the object of which reaction is to prevent and, at the very least, limit the permeability of these sheaths to corrosive fluids such as $H_2S$. It more precisely relates to employing the chemical reaction (1) in the internal sheath to protect the metal layers surrounding this sheath from $H_2S$ by irreversibly neutralizing the corrosive effects of this gas during its diffusion through the sheath.

In this respect, it is known that the barrier layer formed by the sheath manufactured according to the principles of document EP 0 844 429 has a limited lifetime since it loses its effectiveness once all of the reactive compound ZnO added to the material forming the sheath has reacted with corrosive gases. Therefore, by allowing the position of the interface 6 of the front of conversion between ZnO and ZnS in the thickness of the sheath to be detected, the invention allows the consumption of the ZnO in the sheath to be followed in real time, by means of which it is possible to accurately determine the remaining lifetime of the sheath forming the anti-$H_2S$ protective barrier. Thus, the invention allows the protection offered by the limited-permeability sheath described in document EP 0 844 429 to be combined with the ability to monitor, in real time, the effectiveness of the barrier to corrosive gases provided by this layer, allowing its remaining lifetime, and therefore that of the pipe, to be accurately predicted.

The reader may usefully refer to this document, especially as regards the amount of reactive compound to incorporate into the extrudable polymer in order to ensure the sheath thus produced, depending on the properties of the sheath (diameter, thickness, polymer) and on the type of reactive compound used, has the correct permeability to the corrosive gases under given operation conditions.

FIG. 3 shows the spectrum of the ultrasound beam emitted, the spectrum having a central frequency (such as defined by standard NFA 09-323) between 2 and 2.5 MHz and preferably equal to 2.25 MHz. Excessively low frequencies lead to a low attenuation but to the detriment of sensitivity, and if the frequency is too high the attenuation is such that the signal will not pass right through the sheath if it is very thick.

The pulse width, measured at −20 dB (according to the same standard NFA 09-323) is smaller than or equal to 1.5 μs: a short pulse enables correct detection near the outer surface and a good depth resolution. The pulse width is preferably larger than 0.5 μs in order to be powerful enough.

The bandwidth, measured at −6 dB must lie between 1 and 4 MHz and preferably between 1.5 and 3.5 MHz.

The spectrum of the beam emitted must also comprise a sufficiently large number of waves with a low frequency of about 1 MHz the amplitude difference Δ of which, relative to the central frequency, must not be above 30 dB. This is because these low-frequency waves promote the propagation of the emitted beam, of their reduced sensitivity to attenuation in the material of the sheath. The spectrum and the pulse width are directly related and depend on the damping of the transducer.

FIG. 5 illustrates an embodiment for implementing the monitoring method intended to monitor and quantify the progression of the diffusion of gases through the internal sheath of a flexible pipe in operation. In this embodiment, a monitoring section 20 is fitted with an ultrasound transducer 10 and this monitoring section 20 is connected in series to an end-fitting for fastening the pipe at the upper end of the latter.

More precisely, the monitoring section 20, which is symmetrical about its longitudinal axis XX', the latter being coincident with the central axis of the flexible pipe, comprises two connection flanges 21 and 22, respectively fitted at either end of a cylindrical metal cover 23, a seal 24 being used to seal the assembly. These connection flanges 21 and 22 are intended to be brought into contact with pipe end-fittings or with terminal machinery. The pipe portion incorporated into the monitoring section is shown by its carcass 11 and its internal sheath 12, the latter having the reactive compound ZnO dispersed through its thickness. The internal sheath 12 is crimped, at each of its two ends in the section by virtue of parts called crimping cones, 25 and 26, respectively, which slide into and bear against a conical bearing surface of the corresponding connection flanges, 21 and 22, respectively, and bite into the internal sheath 12, the latter being supported, in these locations, by tapered sleeves, respectively 27 and 28. A pressure sheath 12' passing under the sleeves 27 and 28 is placed between the carcass 11 and the internal sheath 12. This pressure sheath 12' is itself crimped at each of its ends via two crimping cones, 29 and 30, respectively, which bite into the pressure sheath 12', the latter being supported by the carcass 11. In this example, the internal sheath 12 filled with reactive compound is separate from the pressure sheath 12', the pressure sheath 12' being, by definition, the first sheath starting from the interior. The invention could naturally be applied to pipes in which these two sheaths are one and the same sheath.

The flexible pipe portion fitted in the monitoring section 20 is for example extracted, during manufacture of the flexible pipe to which the section is intended to be connected in series, from the end of the flexible pipe. This portion extracted from the end of the flexible pipe then has its metal armor layers (pressure vault and tensile armor layers) and its protective external sheath removed in order to be fitted in the monitoring section as explained above. In this way, the monitoring section 20 has a flexible pipe structure that is, as regards the internal sheath to be inspected, identical to that of the flexible pipe to which it is intended to be connected, thus providing a measurement environment, for the ultrasound transducer fitted in the section, that is representative of that of the flexible pipe.

Furthermore, the metal cylindrical cover 23 of the monitoring section 20 is equipped with a set of grooves 31 on its inner surface, at the interface with the outer surface of the internal sheath 12, except in line with the position of the ultrasound transducer 10, so as to simulate the presence of gaps present in the pressure vault. Therefore, the internal sheath 12 of the monitoring section 20 is placed under conditions that are the same as those that would exist if it were surrounded by a pressure vault. The set of grooves 31 is connected by a longitudinal groove 32 to an aperture 33 able to be closed by way of a removable blocking means, the aperture communicating with the exterior, this assembly advantageously forming a circuit for draining gases diffusing through the internal sheath 12, via which the pressure to which the internal sheath 12 in the monitoring section is subjected may be controlled.

The monitoring section 20 may also be equipped with heating means for controlling temperature, not shown, placed substantially around the cylindrical metal cover 23 and allowing the temperature of the flexible pipe portion, and in particular of the internal sheath 12, fitted in the section, to be adjusted and controlled. These means may for example comprise resistive heaters. They may allow, for example, the pipe portion incorporated into the monitoring section to be placed under temperature conditions that are more representative of the least favorable point in terms of the influence of temperature on the diffusion of gases through the internal sheath, which point is typically located near the well head at the bottom of the flexible pipe installation, where the temperature of the transported fluid is at its highest.

Thus, it is possible to reproduce, in the pipe portion in the instrumented monitoring section, a measurement environment, especially in terms of its high pressure and high temperature, that is similar to that encountered by the internal sheath of the flexible pipe, the integrity of which pipe, with respect to the diffusion of corrosive gases through said sheath, is to be inspected by ultrasonography.

Regarding the ultrasound transducer 10, the latter is housed in the cylindrical metal cover 23 and placed a distance h from the outer surface of the internal sheath 12, so as to allow it to detect and observe the progression of the diffusion of gases through the sheath 12 of the pipe portion, according to the principles outlined above. For example, the transducer 10 is screwed into the cylindrical metal cover. It is necessary to ensure the steel cover 23 is sufficiently thick, in line with the ultrasound transducer, to withstand the internal pressure used.

Moreover, a passage 34 is provided allowing a first coupling means to be applied between the front side of the ultrasound transducer and the cylindrical metal cover in which the transducer is housed. In the conventional way, this coupling of the front side of the transducer to the cover may be achieved by injecting a gel- or oil-based coupling medium. The dimensions of the passage 34 will be chosen so as to ensure good transmission of the ultrasound between the transducer and the cylindrical metal cover, while impeding the generation of effects that could interfere with the measurement of the ultrasound. The thickness of the passage 34, in line with the front side of the transducer 10 is an important feature as it determines the thickness of the coupling-medium film that the ultrasound beam has to pass through. In practice, this passage thickness must advantageously be much smaller than half the wavelength used. By way of example, for a transducer central frequency of 2 MHz, the propagation speed of ultrasound in steel being equal to about 6000 m/s, the wavelength in steel is λ=c/N, c being the propagation speed and N being the frequency, i.e. substantially 3 mm. It will therefore, for example, possibly be chosen to couple the front side of the transducer and the cylindrical metal cover with a film of oil having a thickness of about one tenth of a millimeter. As a variant, this coupling could also be obtained by positioning a thin washer made of an elastomer at the bottom of the hole in which the ultrasound transducer is housed.

A second coupling means is also required between the cylindrical metal cover and the outer surface of the internal ZnO-filled sheath 12. This second coupling means is advantageously just the internal pressure generated by the fluid transported by the flexible pipe portion, this pressure being about one hundred bars. Specifically, provided that the cylindrical metal cover has been suitably machined to have a smooth surface finish, the mechanical coupling, under pressure, between the inner surface of the cylindrical metal cover and the outer surface of the internal sheath is alone enough to obtain a clear interface and therefore good coupling, allowing the ultrasonography measurement to be carried out. Thus, the invention advantageously makes use of the high-pressure conditions to which the flexible pipe is subjected in use to achieve this second coupling between the outer surface of the internal sheath and the cylindrical metal cover, which coupling is necessary if the ultrasound measurement is to be carried out correctly.

Thus, by virtue of these means for coupling the front side of the ultrasound transducer 10 to the outer surface of the internal sheath 12, the ultrasound wave generated by the transducer passes, via these coupling means, through the thickness of steel remaining in the cylindrical metal cover, in line with the transducer, before penetrating into the internal ZnO-filled sheath. On return, after reflection from the bottom of the internal sheath, the ultrasound wave takes the same path but in the opposite direction.

Furthermore, to obtain an echogram, such as that shown in FIG. 3, that can be used with a view to monitoring the diffusion of corrosive gases through the sheath, it is advantageous to carefully define the distance h at which the front side of the transducer 10 is located relative to the internal sheath of the pipe portion fitted in the monitoring section. In particular, the distance h must be chosen such that the rebound echo of the ultrasound echoed from the front side of the transducer 10 is sensed after the echo from the sheath bottom, so as not to introduce noise over the echoes that are of interest, especially the echo from the top of the sheath, the echo from the ZnO/ZnS front interface and the echo from the bottom of the sheath. To do this, the distance h is defined in the following way:

$$h \geq e \times \frac{V1}{V2}.$$

Where:

e is the thickness of the internal sheath 12;

V1 is the propagation speed of the ultrasound in the cylindrical metal cover; and V2 is the propagation speed of the ultrasound in the internal sheath.

In practice, V1 is about 6000 m/s and V2 is about 2000 m/s (case of PE), so that the thickness h of steel remaining between the front side of the transducer and the outer surface of the internal sheath must be larger than at least three times the thickness of the sheath in order to meet the aforementioned condition regarding propagation of the waves.

Furthermore, if it is desired to extend the measurement field beyond the internal sheath, as far as the carcass, the thickness of the sacrificial sheath 12' is taken into account so that the rebound echoes on the front side of the transducer arrive after the echo generated by the carcass, so as to obtain a "clean" echogram as far as the carcass.

Moreover, it is desirable to focus the ultrasound wave emitted in order to improve the signal-to-noise ratio of the response of the transducer. The focal point is the point where the ultrasound wave emitted by the transducer exhibits maximum intensity. The intensity gradually decreases with distance from the focal point. The −6 dB focal spot is, by definition, the volume surrounding the focal point in which the intensity of the ultrasound remains at least higher than 50% of the intensity at the focal point. A known means for measuring the size of the focal spot consists in immerging the transducer in a tank filled with water and moving a small metal ball into the field of the transducer, the ball reflecting the ultrasound. For each relative position of the ball and transducer, the amplitude of the ultrasound echo reflected from the ball is recorded, this amplitude being proportional to the intensity of the wave at the point occupied by the ball. By moving the ball along 3 axes so as to map out the entire volume occupied by the ultrasound beam, the position of the focal point and the edges of the −6 dB focal spot can be determined.

Common focused transducers have a structure that is symmetric about the axis of the acoustic beam. The −6 dB focal spot of such sensors is also substantially symmetric about the axis of the acoustic beam, and generally takes the shape of an ellipsoid of revolution. The width of the focal spot, also called the diameter of the focal spot, is measured in the focal plane, i.e. in the plane perpendicular to the axis of the acoustic beam and passing through the focal point. According to the invention, the focal spot is advantageously about a few millimeters in width and ideally is chosen to be, at most, 2 mm to 5 mm in width. The length of the focal spot is measured along the axis of the acoustic beam. According to the invention the length of the focal spot is chosen to cover the entire thickness of the internal sheath 12. In fact, it is preferable to choose a spot length much larger than the thickness of the sheath, and to focus the spot towards or beyond the bottom of the sheath so as to easily cover the entire sheath and to reduce sensitivity to variations in the distance between the transducer and the sheath. The acoustic focus coefficient will be chosen so as to obtain an optimal signal-to-noise ratio for the envisioned application of monitoring the diffusion of corrosive gases through the sheath.

A focus may be obtained using ultrasound lenses; appropriately shaped mirrors; by shaping the piezoelectric transducer, especially if it is a piezocomposite ultrasound transducer; or using an electronically phase-shifted array of elementary transducers (i.e. a phased array).

Figure 6B:
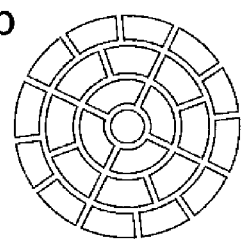

FIGS. 6a and 6b illustrate two possible configurations for such phased arrays, which may be suitable for the ultrasonic transducer 10, i.e. a two-dimensional square pattern and a segmented two-dimensional annular pattern.

Figure 7:
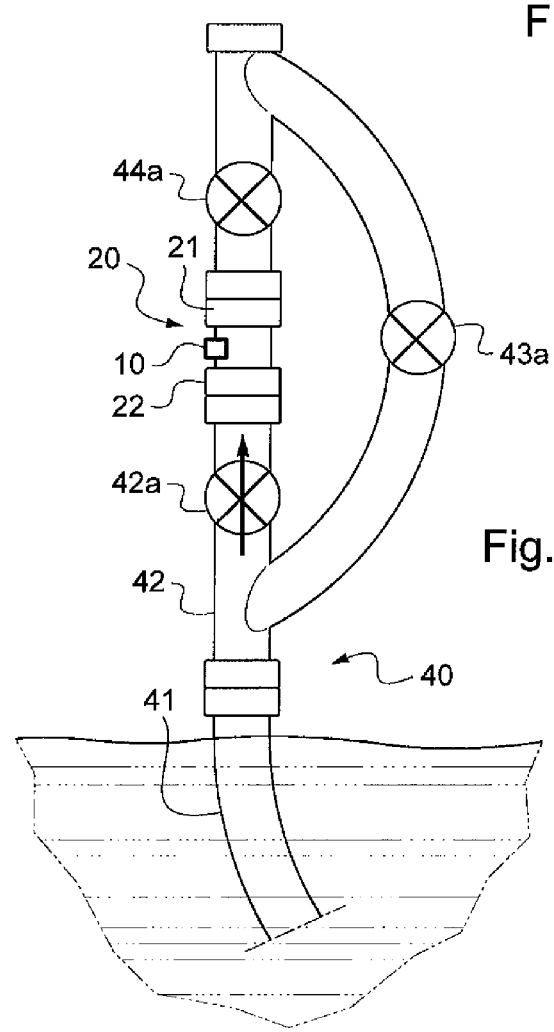
FIG. 7 shows an example of a submarine pipe installation in which the instrumented section is employed according to the invention.

FIG. 7 shows an exemplary configuration for a monitoring section 20, instrumented as explained above, fitted to a flexible pipe installation 40 of the type used in a bottom-to-surface connection between a submarine piece of equipment, such as, for example, a well head, and a surface unit, which may consist of a floating platform or ship. According to this embodiment, the submarine pipe installation 40 comprises a vertical flexible pipe 41 the lower end of which is connected to the well head at the bottom of the sea and the upper end of which opens onto the sea surface; a linking pipe 42, joining the upper end of the vertical flexible pipe 41 and the surface unit, and a by-pass pipe 43 between the upper end of the vertical flexible pipe and the surface unit, in parallel with the linking pipe 42. The monitoring section 20 equipped with the ultrasound transducer 10 for implementing the method of the invention is connected in series with the linking pipe 42 via its two connection flanges 21 and 22 fastened to corresponding fastening end-fittings of the linking pipe. Thus, the ultrasound transducer is easily accessible, which, in particular, makes it easier to connect it to a signal processing unit. Furthermore, valves 42a, 43a and 44a allow the flow of fluid in the fluid circuit formed by the various pipes of the installation to be controlled. In particular, the linking pipe portion incorporating the monitoring section 20 may be isolated from the fluid circuit by closing the valves 42a and 44a, the valve 43a being opened to allow the fluid to flow through the by-pass pipe 43. In this way, work may be carried out on the monitoring section 20 in order to maintain and/or test the operation of the transducer.

As a variant, the ultrasound transducer may also be incorporated directly into one of the fastening end-fittings of the flexible pipe. Specifically, it is possible to house the ultrasound transducer under the armor layers behind the end-fitting, on the flexible pipe side. It is also possible to lengthen the end-fitting on the flange side so as to extend the internal sheath beyond the anchoring zone of the armor layers, and to place the ultrasound transducer in line with the extended zone.

As regards rigid pipes comprising an internal liner, it is possible to instrument them by directly placing the ultrasound transducer on the exterior of the metal tube surrounding the liner, said metal tube possibly then being equivalent to the cylindrical metal cover (23) in FIG. 5.

The invention claimed is:

1. A method for monitoring a tubular pipe which transports hydrocarbons containing corrosive gases, the pipe comprising:
an internal polymer sheath through which the hydrocarbons pass, the sheath having an inner surface past which the hydrocarbons pass and having an opposite radially outer surface and having a thickness between the inner and outer surfaces, the sheath being comprised of a polymer through which the corrosive gases are liable to diffuse radially from the inner surface through the thickness toward the outer surface thereof;
reactive-compound elements dispersed throughout the thickness of the sheath between the inner and the outer surfaces thereof, and the reactive-compound elements reacting with the corrosive gases which diffuse through the sheath such that the reactive-compound elements are operable to neutralize the corrosive gases diffusing through the sheath in a neutralizing reaction;
the incorporated reactive-compound elements and their neutralizing reaction with the corrosive gases and the radial diffusion of the corrosive gases forming a first layer radially outward from the inner surface of the sheath in the thickness of the sheath, and the first layer is where the reactive-compound elements have reacted with the corrosive gases, such that the first layer gradually extends further radially through the thickness of the sheath from the inner surface as reactions occur, and also forming a second layer of the sheath radially outward of the first layer and toward the outer layer and occupying a residual thickness of the sheath with the reactive-compound elements dispersed in it, wherein the reactive-compound elements in the second layer have not reacted with the corrosive layers, such that the second layer extends from in between the first layer and the second layer and extends radially outwardly through the residual thickness toward the outer surface of the sheath;
the method comprising:
passing the hydrocarbons containing corrosive gases through the internal sheath and in contact with the inner surface thereof for additionally causing radial diffusion of the corrosive gases outwardly through the thickness of the sheath and for causing neutralizing of the corrosive gases by the reactive-compound elements in the sheath, and thereby developing an interface layer in the thickness of the sheath between the first and the second layers;
determining the position of the interface between the first and second layers by application of ultrasound to the internal sheath and sensing the ultrasound applied to the sheath for measuring in real time the progression of the diffusion of corrosive gases through the thickness of the internal sheath by determining the position of the interface.

2. The monitoring method as claimed in claim 1, further comprising:
the application of ultrasound comprises causing emitting of an ultrasound beam from the outer surface of the internal sheath and in a radial direction toward the interior of the pipe in a manner which causes the ultrasound beam to pass into the outer surface, and through the thickness of the internal sheath between the outer surface and the inner surface of the sheath; and
collecting ultrasonic waves reflected from within the thickness of the sheath by the interface, wherein the reflective waves are collected in the form of signals, and processing the signals from the interface for determining the position of the interface in the thickness of the internal sheath.

3. The method as claimed in claim 2, wherein the central frequency of the ultrasound beam lies in the range between 1.5 and 3 MHz, the pulse width, measured at −20 dB, lies between 0.5 and 1.5 µs, and the bandwidth, measure at −6 dB, lies between 1 and 4 MHz; and
the method further comprising using a spectrum comprising a sufficiently large number of waves with a low frequency of about 1 MHz having an amplitude difference relative to the central frequency of not less than 30 dB.

4. The method as claimed in claim 2, further comprising focusing the shape of the ultrasound beam to have a beam focal point positioned toward or beyond the inner surface of the internal sheath.

5. The method as claimed in claim 4, further comprising using a square-shaped or annular two-dimensional array of elementary transducers for shaping the beam.

6. The method as claimed in claim 5, further comprising controlling the ultrasound beam using an electronic phase-shift technique.

7. The method as claimed in claim 1, further comprising using a piezocomposite ultrasonic transducer for emitting ultrasonic waves.

8. The method as claimed in claim 7, further comprising shaping the piezocomposite component of the transducer for achieving focus of the ultrasound beam.

9. The method as claimed in claim 1, wherein the reactive-compound is selected from the group consisting of ZnO, PbO, CuO, CdO, NiO, $SnO_2$ and $MoO_3$.

* * * * *